United States Patent [19]
Cole et al.

[11] Patent Number: 5,350,378
[45] Date of Patent: Sep. 27, 1994

[54] POSTERIOR EXTERNAL PELVIC FIXATOR

[76] Inventors: J. Dean Cole, 530 E. Central, Apt. 1005, Orlando, Fla. 32801; Daniel F. Justin, 4544 Tescott Dr., Orlando, Fla. 32817

[21] Appl. No.: 64,589

[22] Filed: May 19, 1993

[51] Int. Cl.$^5$ .............................................. A61B 17/60
[52] U.S. Cl. ...................................................... 606/57
[58] Field of Search ..................... 606/54, 53, 59, 86, 606/96, 105

[56] References Cited

U.S. PATENT DOCUMENTS

| | | | |
|---|---|---|---|
| 2,035,952 | 3/1936 | Ettinger | 606/59 |
| 2,080,802 | 5/1937 | Anderson | 606/54 |
| 4,292,964 | 10/1981 | Ulrich . | |
| 4,361,144 | 11/1982 | Slatis et al. . | |
| 4,815,455 | 3/1989 | Kim . | |
| 5,108,397 | 4/1992 | White . | |
| 5,196,012 | 3/1993 | Malka . | |
| 5,207,688 | 5/1993 | Carol | 606/130 |

FOREIGN PATENT DOCUMENTS 1149960  4/1985  U.S.S.R. ............................. 606/54

*Primary Examiner*—Tamara L. Graysay
*Attorney, Agent, or Firm*—Allen, Dyer, Doppelt, Eranjola & Milbrath

[57] ABSTRACT

A pelvic fixation device and method for the initial stabilization and reduction of pelvic ring fractures, includes an adjustable radiolucent frame, first and second fixation pins connected to the frame in spaced relation relative to each other for fixing the frame to the posterior pelvis on opposite sides of the fracture, an adjustment mechanism for moving the first and second fixation pins relative to each other for stabilizing and reducing the pelvic fracture, and an adjustable spacer for adjusting the distance between the device and the patient.

4 Claims, 2 Drawing Sheets

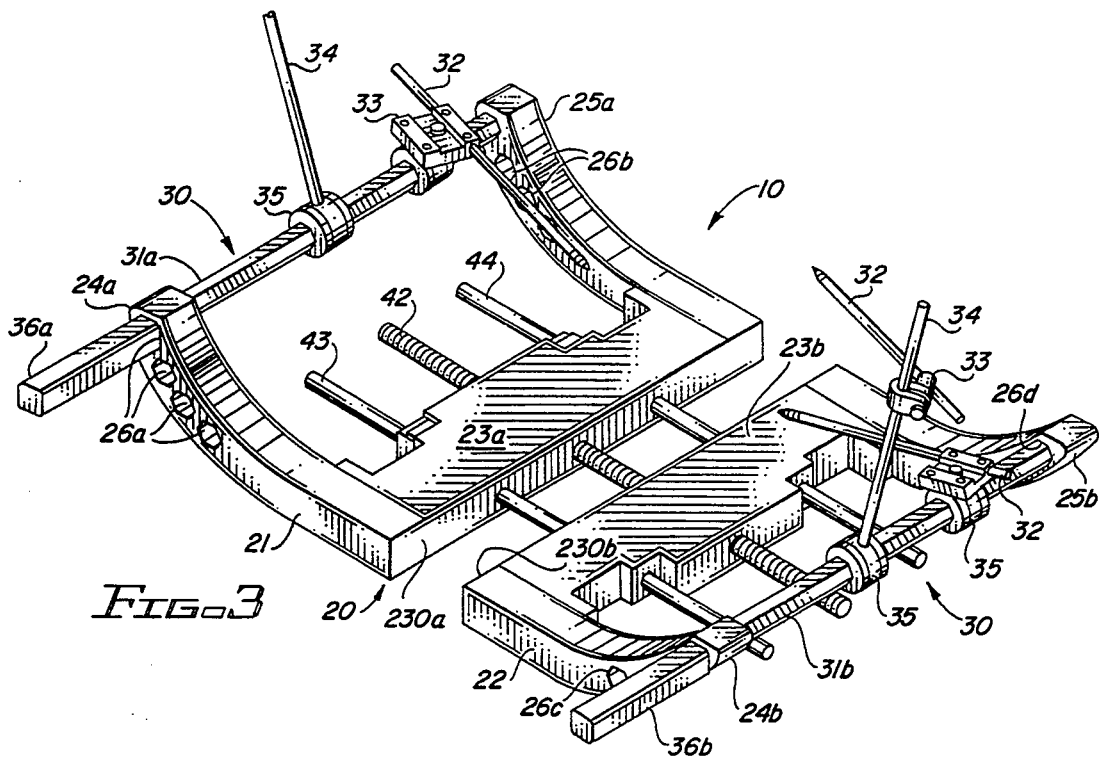
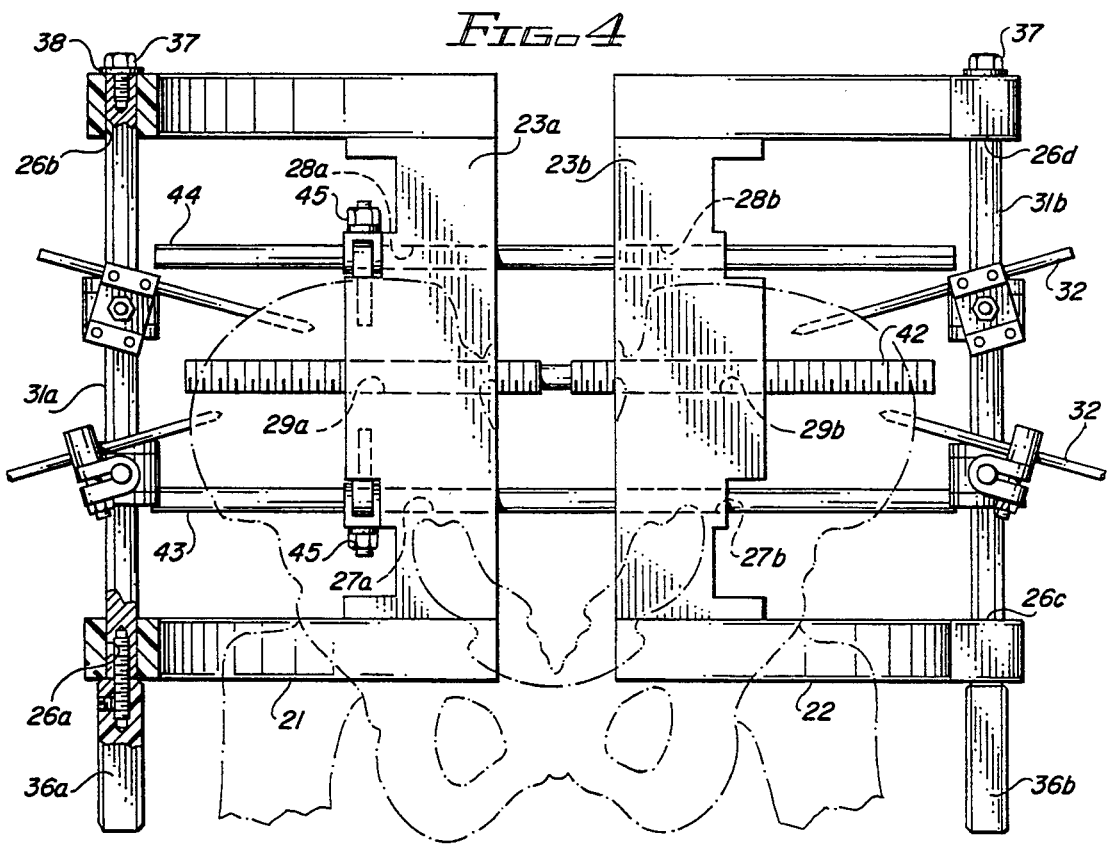

POSTERIOR EXTERNAL PELVIC FIXATOR

FIELD OF THE INVENTION

The invention generally relates to an apparatus and method useful for the initial stabilization and reduction of pelvic ring fractures and, more particularly, to an adjustable, radiolucent frame that is mounted to the posterior side of the pelvis and secured to the ilium with bone pins.

BACKGROUND OF THE INVENTION

Fractures of the pelvis arise from severe blunt impacts on the pelvic girdle, which occur most often, for example, in traffic accidents, free falls and industrial accidents. Pelvic fractures tend to be serious injuries which involve massive blood loss and the time between the initial fracture and surgical intervention is critical. It has been shown that external fixation plays a major role in reducing the bleeding during the acute phase of these pelvic fractures.

Once past the acute phase of a pelvic fracture, internal pelvic fixation is typically used to provide stabilization for the pelvic ring fractures as they heal. However, these internal pelvic fixation surgical procedures are generally undertaken in well staffed and well equipped surgical trauma centers and then only as part of a post-trauma situation. When external fixation devices are attached to the fractured pelvis, the broken parts may be aligned and firmly held in an appropriate position until the patient either can be transported to a surgical trauma center, or is stable enough to undergo internal fixation surgical procedures.

The accidents that cause pelvic fractures tend to occur at distances remote from surgical centers that are able to perform the required internal fixation procedures. Thus, the patient needs to be transported a distance and/or stabilized prior to surgery. The existing external fixation devices used for pelvic fractures are mounted anteriorly, cumbersome to handle, and frequently difficult to attach. Additionally, they are not radiolucent, making it difficult to obtain the necessary pelvic x-rays prior to surgery, and most often are not intended for use solely on the pelvis.

An external pelvic fixation device is needed that is radiolucent and adjustable so as to provide the ability to place bone pins in a variety of planes and positions on a fractured pelvis. A pelvic fixation device is also needed that can be quickly and simply mounted posteriorly on a patient at an accident scene or in a hospital trauma center. This will allow for rapid initial stabilization and reduction of the pelvic fracture until the patient can be transported to a surgical trauma center and stabilized with internal fixation of the fracture.

SUMMARY OF THE INVENTION

The present invention provides a radiolucent pelvic fixation device for initially stabilizing and reducing pelvic ring fractures. The device is mechanically uncomplicated and relatively easy to install. The ease of its use can prevent the massive blood loss that often results from this type of trauma.

The pelvic fixation device of the present invention includes a frame, pins for connecting the frame to a patient's pelvis, an adjustment mechanism for adjusting the frame for a proper fit after it is fixed, and a cushion between the frame and the patient. The frame is formed with two sections, each section being generally U-shaped with a straight connecting portion and curving end portions. The two sections are oriented so that their respective straight connecting portions are placed back-to-back adjacent to each other. Each end portion includes a plurality of openings for receiving rods that hold fixation pins.

The pins are connected through the rods in the end portions for connecting the frame to the posterior side of the pelvis on opposite sides of a fracture. The rods are mounted so they are oriented parallel to the flat connecting portions of the frame. Bone pins are mounted on the rods such that they can be positioned in any of a variety of planes and positions relative to the pelvis for ease of installation.

The frame sections can be adjusted inward and outward relative to each other, through movement of a drive screw connected between the frame sections. Guide rods are positioned between the frame sections for maintaining their alignment as they are moved. An inflatable cushion is placed between the patient and the middle section of the frame to maintain proper spacing between the patient's pelvis and the frame.

The device is installed by placing a patient on the cushion which has been placed on the open frame The cushion is inflated in order to place the patient in the proper position for inserting the bone pins. Self-drilling bone pins are then placed through pin clamps and into the desired location in the ilium of the patient's pelvis. The bone pins are then secured to the rods by use of spool pieces and set screws. Once the pins are secured on the rods, the drive screw is turned manually, bringing the two frame sections together and closing the fracture in the pelvic ring. After the fracture is closed, the cushion is inflated or deflated as needed to allow for spacing adjustment of the patient relative to the frame.

The fixation device, in accordance with the invention, is mounted posteriorly with the patient in the supine position. This allows the patient to be comfortably transported and permits surgical access to the peritoneal space with an anterior approach. The device is modular, so that it can be disassembled and placed in a compact container for use in emergency vehicles, trauma centers and hospital emergency rooms. Once the patient is stabilized with the device of the present invention, he or she can be easily transported from the emergency site to an appropriate surgical setting for internal fixation of the fracture.

BRIEF DESCRIPTION OF THE DRAWINGS

The objects, advantages and features of the invention will become more apparent when the detailed description of exemplary embodiments is considered in conjunction with the appended drawings, in which:

FIG. 3 is a perspective view of the pelvic fixation device of the present invention; and FIG. 4 is a top plan view of the device of FIG. 3, showing an attachment to the pelvis of a patient.

DETAILED DESCRIPTION OF AN EXEMPLARY EMBODIMENT

Figure 1:
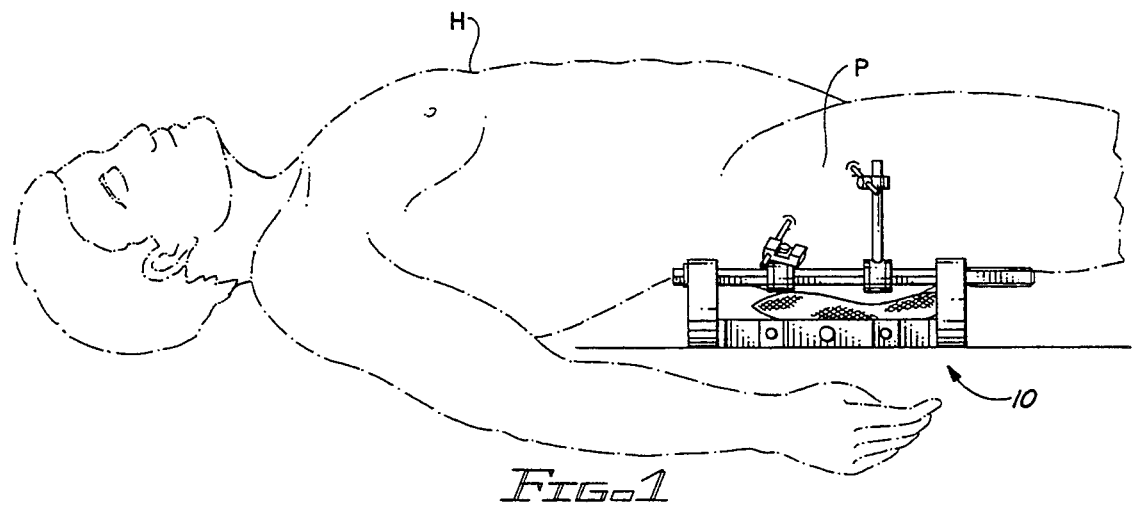
FIG. 1 is partial schematic view of the pelvic fixation device of the present invention as applied to a patient's body.
Figure 2:
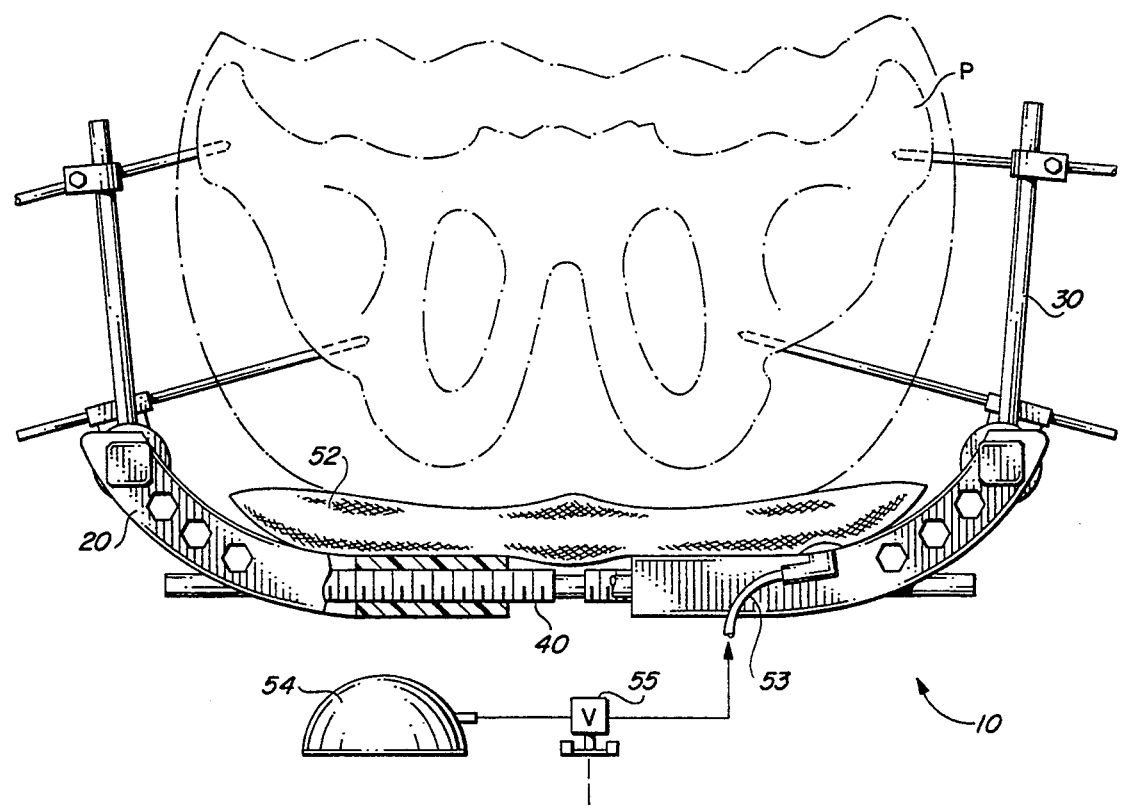
FIG. 2 is partial schematic view of the device of the present invention, as viewed toward the mid-line of the body.

Referring to FIG. 1, reference letter H identifies a human patient in the supine position on which a pelvic fixation device 10 of the present invention is mounted on the posterior side of pelvis P. As illustrated in FIG. 2, the pelvic fixation device 10 includes a frame 20, a fixation mechanism generally designated by reference numeral 30 for connecting the frame to the posterior side of the pelvis P on opposite sides of a fracture, an adjustment mechanism generally designated by reference numeral 40 for moving the fixation system relative to each other in order to stabilize and reduce the pelvic fracture, and an inflatable cushion generally designated by reference numeral 52 which is useful for installing the device as described in greater detail below.

In a preferred embodiment, the frame 20 is formed of a radiolucent or radiotransparent plastic material such as one known to those skilled in the art as Ultem TM a polyether imide resin manufactured by General Electric (Pittsfield, Mass). The frame 20 has first and second sections 21 and 22, as shown in FIG. 3, which are identical to each other. Sections 21,22 are both generally U-shaped with a straight connecting portion and curving end portions. The connecting portion of the first section 21 is designated 23a and the end portions 24a and 25a. The connecting portion of the second section is designated 23b and the end portions 24b and 25b. The frame sections 21 and 22 are oriented so that their connecting portions 23a and 23b are positioned with their respective backs 230a and 230b facing each other.

Each of the end portions 24a, 25a of the frame section 21 and end portions 24b, 25b of the frame section 22 includes a plurality of openings 26a,b,c and d, which extend generally parallel to the connecting portions 23a and 23b. The openings 26a,b,c,d receive the fixation mechanism 30 as shown in FIG. 3.

As illustrated in FIG. 4, the connecting portions 23a,b of the frame sections 21 and 22 include coextensive openings 29a, 29b for receiving a drive screw 42 for moving the frame sections 21 and 22 relative to each other as described in greater detail below. The frame sections 21 and 22 also include coextensive guide openings 27a, 27b and 28a, 28b for receiving guide rods 43,44, respectively.

The fixation mechanism 30 for frame sections 21 and 22 includes rods 31a and 31b that is inserted into the openings 26a,b,c,d in the frame sections 21 and 22. In a preferred embodiment, the rods 31 are hexagonally-shaped bars formed of a composite material of a polymer and carbon fibers. As illustrated in FIGS. 3 and 4, the rods 31a,b extend parallel to the connecting portions 23a,b of the frame sections 21 and 22 so that rods 31a,b extend parallel to the pelvis P of a patient when the pelvic fixation device 10 is mounted to the posterior side of the pelvis P as shown in FIG. 1.

The frame sections 21 and 22 are connected to the patient's pelvis through bone pins 32 that are retained on adjustable pin clamps 33 and/or extensions 34 connected to spool pieces 35 that are slidable along the rods 31a,b. In a preferred embodiment these components are part of the Smith & Nephew Richards Hex Fix ® System, an orthopedic fixation (Smith and Nephew Richards, Inc., Memphis, Tenn.). They allow for the placement of the bone pins 32 in an infinite number of planes and positions on the pelvis P.

By use of the pin clamps 33, extensions 34 and spool pieces 35, the pins 32 can be placed in an appropriate position along the rods 31a,b depending upon where the pins 32 are to be inserted into the ilium of the fractured pelvis P. The number and type of bone pins 32 and other component pieces placed on the rods 31a,b are dependent upon the location of the fracture in the pelvic ring.

The distance between the rods 31a,b and the pelvis P is adjusted by mounting the rods 31a,b in a different set of openings 26a,b,c,d in the end portions 24a,b and 25a,b. In a preferred embodiment, the rods 31a,b have a handles 36a,b at one end (see FIG. 4) and an opening for receiving cup screws 37a,b and washers 38 at the other end for holding the rods 31a,b in the openings 26a,b,c,d. The rods 31a,b are inserted through the openings 26a,b,c,d and secured in place by the handles 36a,b at one end and the cup screw 37a,b and washers 38 at the other end.

The drive screw 42 is used to move the frame sections 21, 22 relative to each other to adjust the device to the patient. The drive screw 42 has right and left screw threads on opposite ends for moving the frame sections 21 and 22 inward and outward relative to each other. In a preferred embodiment, the drive screw 42 is formed of a radiolucent or radiotransparent plastic material such as Ultem TM, previously described. The drive screw 42 is mounted in the threaded openings 29a,b of the connecting portions 23a,b and engages the cooperating internal threads of the openings 29a,b. When the drive screw 42 is turned in one direction, the frame sections 21,22 move toward each other. When the drive screw 42 is turned in the opposite direction, the frame sections 21,22 move away from each other.

The guide rods 43,44 are also formed of a composite polymer/carbon fiber material. The guide rods 43,44 are inserted through the guide openings 27a,b and 28a,b respectively for providing stability and alignment of the frame sections 21,22 as they are moved relative to each other. As shown in FIG. 4, a locking clamp 45 is provided to secure the guide rods 43,44 to the frame section 21.

As illustrated in FIG. 2, the cushion 52 is inflated by a pump 54 that is connected to the cushion 52 through a one-way valve 55. Air enters the cushion 52 via an air hose 53, passing through the valve 55, which controls the inlet and outlet of air into the cushion 52. The cushion 52 is inflated to a desirable height in order to provide proper placement of the bone pins 32 before they are inserted into the pelvis P. After the bone pins 32 are inserted and the frame 20 is properly adjusted, the amount of air in the cushion 52 is adjusted to place the patient in the proper position relative to the frame 20.

As shown in FIG. 1, the pelvic fixation device 10 is mounted posteriorly with the patient in the supine position. After the frame is opened by spacing the frame sections 21,22 apart from each other, the cushion is placed in the center of the frame. After the patient is positioned upon the cushion it is inflated in order to place the pelvis in proper position relative to the fixation pins. The pins are then inserted into the ilium and secured to the rods.

The cushion is either inflated or deflated if the patient requires additional positioning. The drive screw is rotated, by manually turning either one of the ends of the drive screw, to move the frame sections together. This provides final adjustment to the inserted bone pins and further compresses and reduces the pelvic ring fracture. The inflatable cushion may require a final spacing adjustment to provide the proper spacing of the patient relative to the frame.

The pelvic fixation device of the present invention provides rapid initial stabilization and reduction of pelvic ring fractures. The radiolucent, adjustable frame can be completely disassembled and placed in a small container suitable for storage in hospital emergency rooms, trauma centers and emergency vehicles. The device mounts posteriorly with the patient in the supine position which allows for easier placement of the bone pins, access to the peritoneal space with an anterior approach, and easier transportation of the patient from an emergency site to a surgical setting for internal fixation of the fracture.

The foregoing disclosure and description of the invention are illustrative and exemplary thereof, and various changes in the size, shape and materials, as well as in the details of the illustrated construction may be made without departing from the spirit of the invention.

What is claimed is:

1. A pelvic fixation device for stabilization and reduction of pelvic ring fractures of a patient, comprising:
    a frame formed of a radiolucent material, the frame including first and second sections, each one having generally a U shape with a relatively straight connecting portion, each connecting portion having a back, and curving end portions, the sections being oriented so that the backs of the respective connecting portions face each other, and the end portions including a plurality of openings extending parallel to the connecting portion of the frame for providing adjustable placement of the fixation means;
    first and second fixation means connected to the frame in spaced relation relative to each other for fixing the frame to the posterior pelvis on opposite sides of the fracture;
    adjustment means for moving the first and second fixation means relative to each other for stabilizing and reducing the pelvic fracture; and
    an adjustable spacing means for adjusting the distance between the frame and the patient.

2. A pelvic fixation device for stabilization and reduction of pelvic ring fractures of a patient, comprising:
    a frame formed of a radiolucent material, the frame having a first and a second section;
    first and second fixation means connected to the frame in spaced relation relative to each other for fixing the frame to the posterior pelvis on opposite sides of the fracture;
    adjustment means for moving the first and second fixation means relative to each other for stabilizing and reducing the pelvic fracture, the adjustment means including a drive screw means having right and left screw threads for moving the first and the second sections of the frame back and forth relative to each other; and
    an adjustable spacing means for adjusting the distance between the frame and the patient.

3. A pelvic fixation device for stabilization and reduction of pelvic ring fractures of a patient, comprising:
    a frame formed of a radiolucent material, the frame having a first and a second section;
    first and second fixation means connected to the frame in spaced relation relative to each other for fixing the frame to the posterior pelvis on opposite sides of the fracture;
    adjustment means for moving the first and second fixation means relative to each other for stabilizing and reducing the pelvic fracture; and
    adjustable spacing means, including an inflatable cushion, a pump, and a one-way valve for the inlet and outlet of air for providing spacing adjustment of a patient relative to the frame.

4. A method of stabilizing and reducing pelvic ring fractures of a patient, comprising the steps of:
    providing a pelvic fixation device comprising:
        a frame formed of radiolucent material;
        first and second fixation means connected to the frame in spaced relation relative to each other for fixing the frame to a posterior portion of a patient's pelvis on opposite sides of the pelvic ring fracture;
        adjustment means for moving the first and second fixation means relative to each other; and
        adjustable spacing means positioned upon the frame for adjusting the distance between the frame and the patient;
    positioning the patient in a supine position on the adjustable spacing means and adjusting the spacing means to place the patient in a desired vertical position;
    placing the first and the second fixation means into opposite sides of the posterior portion of the patient's pelvis;
    adjusting the adjustment means to move the first and the second fixation means to stabilize and reduce the pelvic ring fracture; and
    readjusting the adjustable spacing means to move the patient relative to the frame.

* * * * *